Figure 3:
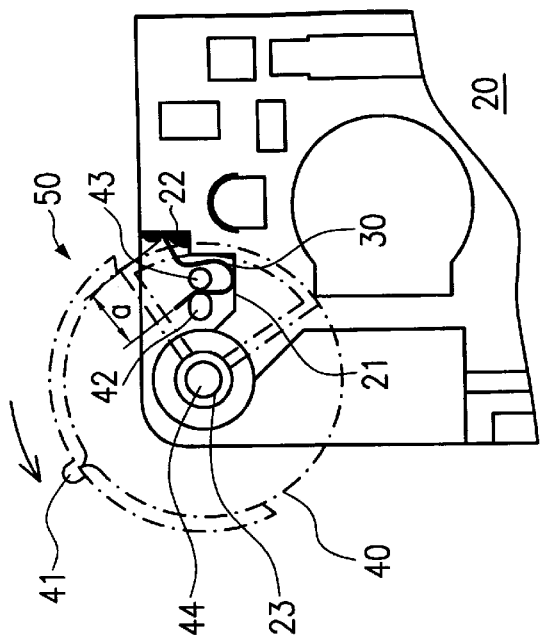

United States Patent [19]
Steinel, Jr.

[11] Patent Number: 6,101,315
[45] Date of Patent: Aug. 8, 2000

[54] ELECTRIC DEVICE FOR EVAPORATING SUBSTANCES

[75] Inventor: Heinrich Wolfgang Steinel, Jr., Bad Woerishofen, Germany

[73] Assignee: Steinel GmbH & Co. KG, Herzebrock-Clarholz, Germany

[21] Appl. No.: 09/242,497

[22] PCT Filed: Aug. 27, 1997

[86] PCT No.: PCT/EP97/04675

§ 371 Date: Apr. 1, 1999

§ 102(e) Date: Apr. 1, 1999

[87] PCT Pub. No.: WO98/10453

PCT Pub. Date: Mar. 12, 1998

[30] Foreign Application Priority Data

Sep. 4, 1996 [DE] Germany ............ 961 14 200

[51] Int. Cl.[7] .......... A01G 13/06; A61M 16/00; H01H 19/58; H01H 9/00
[52] U.S. Cl. .......... 392/386; 392/390; 200/292; 200/11 DA
[58] Field of Search .......... 392/390, 391, 392/392, 394, 395; 200/6 R, 6 C, 16 C, 16 D, 11 A, 11 E, 11 G, 11 TW, 553, 557, 560, 5.62, 564, 292, 336, 339

[56] References Cited

U.S. PATENT DOCUMENTS 3,558,834  1/1971  Zielke .................... 200/292
3,742,171  6/1973  Howe .................... 200/296
5,570,777  11/1996  Skarivoda ............. 200/292

FOREIGN PATENT DOCUMENTS 0 362 397   4/1990   European Pat. Off. .
1 532 608   12/1968  France .
12 53 791   11/1967  Germany .
16 65 063   10/1970  Germany .
22 09 088   9/1973   Germany .
2 285 885   7/1995   United Kingdom .

*Primary Examiner*—Sang Paik
*Attorney, Agent, or Firm*—Darby & Darby

[57] ABSTRACT

An electric device for evaporating substances, comprising a housing, a printed circuit board supported in said housing and used for an electric heating element, and a toggle switch including an operating element which is adapted to be pivoted by a defined angle. The toggle switch is provided with an integral strip-shaped sheet-metal spring serving simultaneously as a switching element for interrupting and for establishing an electrically conductive connection between two contacts and as a resilient element holding the switching element at two stable switching positions. The strip-shaped sheet-metal spring has two end pieces, one end piece being coupled to the operating element and the other end piece abutting directly on one of the two contacts. Furthermore, the strip-shaped sheet-metal spring includes a ¾-circular bend which is brought into contact with the other contact by pivoting the operating element.

7 Claims, 2 Drawing Sheets

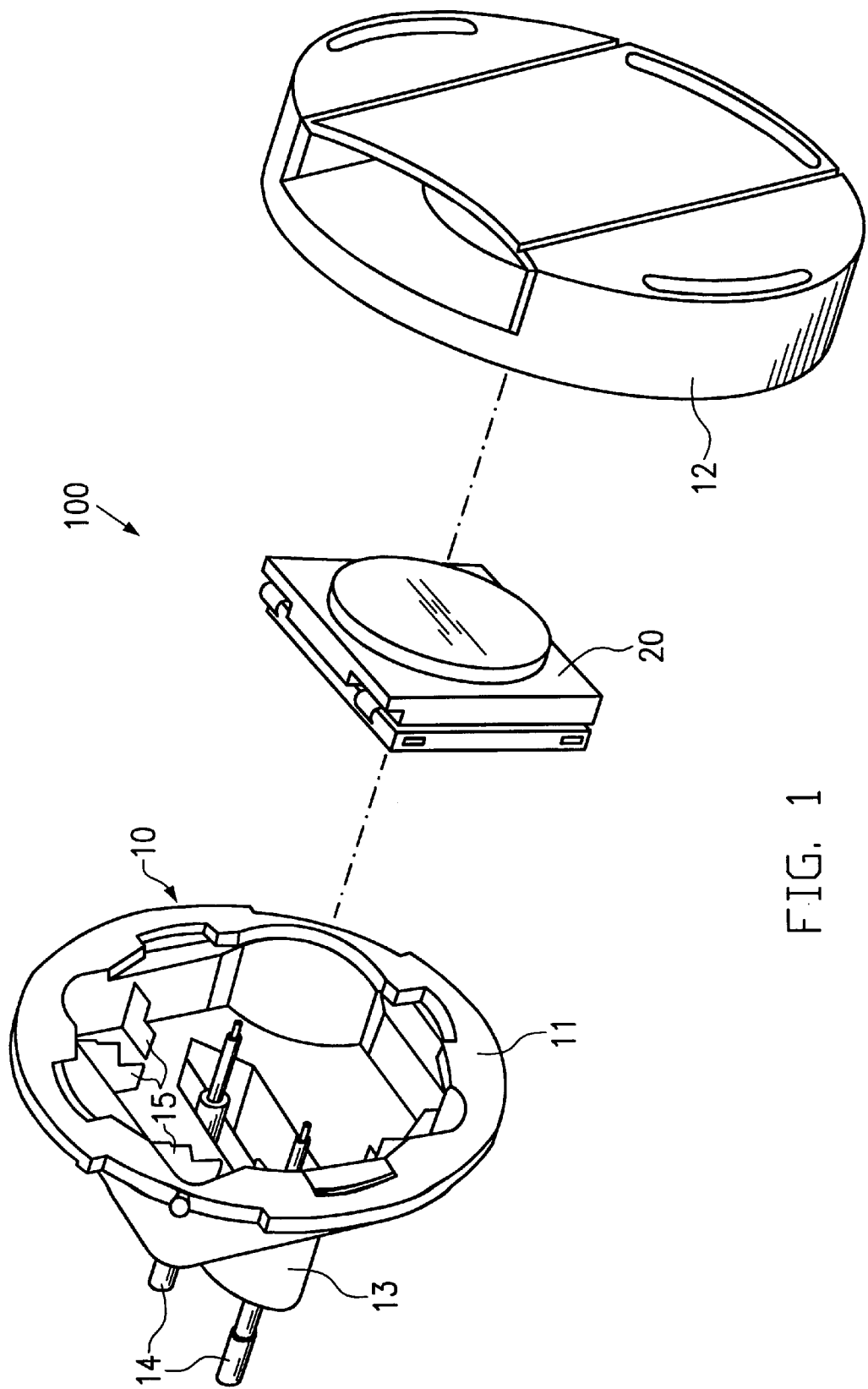

ELECTRIC DEVICE FOR EVAPORATING SUBSTANCES

The present invention refers to an electric device for evaporating substances, perfumes or the like, according to the generic clause of patent claim 1.

Such a device has become known from EP 362 397 A1. It includes a toggle switch with two stable switching positions for switching the device on and off, one of said switching positions being normally the ON position and the other one the OFF position. Such conventional toggle switches comprise an operating element for operating a switching element which interrupts and interconnects two switching contacts. The operating element cooperates with a resilient element in such a way that two stable end positions for the switching element are obtained, the intermediate positions being unstable. The above-mentioned components of the toggle switch are mounted in a toggle switch housing, connection lugs, which are connected to the switching contacts, projecting beyond said housing. For fastening the toggle switch to the housing of the device, the toggle switch housing has resilient detent projections, protrusions or the like, which are adapted to be snapped in position in an opening provided in the housing wall.

These conventional toggle switches are considered to be disadvantageous insofar as they are composed of a large number of individual components which must either be mounted by troublesome manual labour or assembled by means of extremely complicated assembling devices. This results in high production costs. In addition, for electrically connecting the switch, it is necessary that pigtail leads are soldered onto the connection lugs of the switch, and this results in an increase in the production costs for the electric devices using such switches.

Furthermore, EP 696 457 A1 discloses an electric device for evaporating substances which has a switching means integrated in the attachment plug, said switching means consisting of two rotating joint members which are adapted to be brought into engagement with one another so as to establish an electric connection between the attachement plug contacts and an electric switching component.

Although the use of pigtail leads is no longer necessary in the case of this electric device, the production of the rotating joint members is still comparatively complicated. In addition, the operational comfort of the switching means is less high than that of a toggle switch where only two stable switching positions exist. The operator is, however, compelled to rotate the rotating joint members until a locking position has been found. Electric devices including a toggle switch are therefore more readily accepted because of their higher operational comfort.

Hence, it is the object of the present invention to further develop an electric device of the type in question, which includes a toggle switch, in such a way that it has a simple structural design comprising a small number of components and that it can be produced at a reasonable price.

This object is achieved by an electric device having the features of patent claim 1.

The idea underlying the device according to the present invention is that the switching element and the resilient element are implemented as an integral strip-shaped sheet-metal spring, one end piece of the strip being directly coupled to the operating element and the other end piece abutting on one of the contacts. Due to the fact that the strip-shaped sheet-metal spring includes an approximately ¾-circular bend, it can simultaneously fulfil the function of the switching element establishing the contact as well as the function of the resilient element. This reduces the number of individual components included in the toggle switch and, at the same time, the material and mounting costs for the electric device.

In accordance with a preferred embodiment, one end piece of the strip-shaped sheet-metal spring is held between two driving pins arranged on the operating element. When the switch is being assembled, the strip-shaped sheet-metal spring can simply be forced into the gap between the driving pins. The operating element is then simultaneously used as a mounting tool when the switch is being assembled.

In accordance with a preferred embodiment of the electric device, the other end piece of the strip-shaped sheet-metal spring is provided with a semicircular opening snapped into locking engagement with a suitable detent projection of one of the contacts. Such snap-in connections can be mounted rapidly and without any difficulties.

In accordance with a preferred embodiment of the strip-shaped sheet-metal spring, the two ends of said sheet-metal spring are bent off by approx. 90° at the ends of the approx. ¾-circular bend.

The operating element is preferably supported in a reception opening of the printed circuit board via a pivot pin formed thereon, whereby said toggle switch can directly be attached to the printed circuit board in a particularly simple manner. This also has the effect that a separate toggle switch housing, which is normally used in the case of conventional toggle switches, is no longer necessary.

Furthermore, it will be advantageous when a central slot extending in the axial direction is provided at the free end of the pivot pin for forming two semicylindrical end pieces. The operating element can be snapped in position in the reception opening of the printed circuit board in this way, and this will facilitate the assembly of the switch.

In accordance with a preferred embodiment of the present invention, the electric printed circuit board is supported in the housing in such a way that the operating element partially passes through an opening formed in said housing. The housing will then act as a mechanical guide means for the pivotable operating element.

The contacts, which are adapted to be connected via the switching element, are preferably arranged directly on the printed circuit board. It is therefore no longer necessary to provide additional connection contacts on the printed circuit board which must be connected to the contacts of the toggle switch via flexible leads in the case of the prior art.

Figure 4:
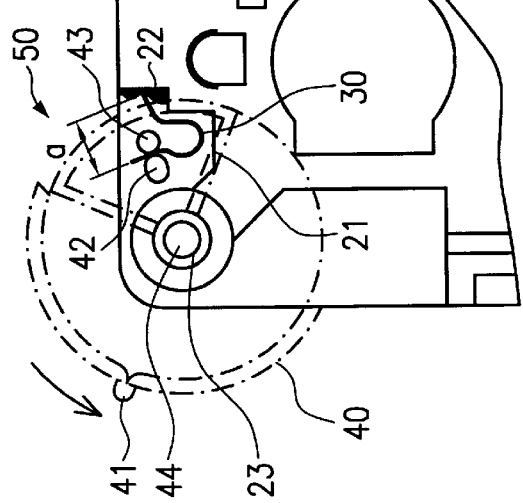
Figure 2:
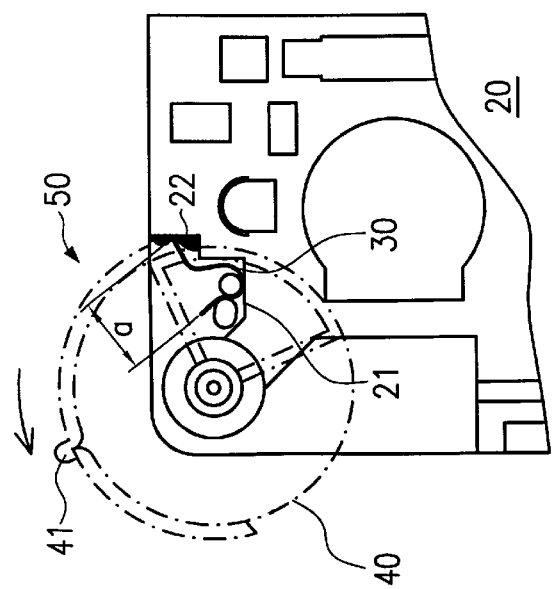

For making the present invention more easily understandable, a preferred embodiment of the device will now be described making reference to the accompanying figures, in which FIG. 1 shows a perspective exploded view of the device according to the present invention, FIG. 2 shows the toggle switch of the device according to FIG. 1, which is secured to the printed circuit board, at its closed position, FIG. 3 shows the toggle switch of FIG. 2 at an unstable position a short time before the conductive connection between two contacts is interrupted, and FIG. 4 shows the toggle switch at the open, stable position.

Making reference to FIG. 1, the electric device 100 comprises a two-part housing 10 and an electric printed circuit board 20 supported in said housing and consisting of a stamped sheet metal component embedded in plastic material by injection moulding. The housing comprises a connecting part 11 and a cover 12 which is adapted to be fastened thereto.

The connecting part 11 includes a projecting connector base 13 which is provided at the rear outer surface thereof and from which two connecting pins 14 project. The connector base and the connecting pins are shaped such that they are suitable to be connected to a standardized wall socket or table socket. On the inner side of the housing of the connecting part retaining webs 15 are formed, which serve to retain the electric printed circuit board 20.

The cirumferential rim of the connecting part 11 has formed therein an opening 16 through which a toggle switch, which is not shown, partially passes, said toggle switch being adapted to be operated from outside by an operator.

The cover 12 is adapted to be secured to the connecting part 11 by means of detent projections and the circumferential edge thereof is provided with an opening for inserting a tray, not shown, consisting of plastic or of metal, e.g. aluminium, into a pocket which is formed in said cover and which contains the substance to be evaporated. The cover is also provided with ventilation openings for permitting air to circulate through the interior of the housing.

FIG. 2 to 4 show a toggle switch which is generally designated by reference numeral 50. The toggle switch is mounted in a corner area of the printed circuit board 20. For this purpose, said corner area is implemented as an eyelet 23 followed by a lateral approximately U-shaped opening. In the base area and on a side leg of said U-shaped opening, a section of a respective contact 21, 22 projects. These contacts are electrically connected to each other through a strip-shaped sheet-metal spring 30 in the closed condition of the switch (FIG. 2), whereas they are isolated from each other in the open condition of the switch (FIG. 4). The strip-shaped sheet-metal spring is preshaped such that it defines a ¾-circular bend which is followed by end pieces which are bent off by approx. 90°.

For operating the strip-shaped sheet-metal spring 30, an operating element 40 is provided, which has approximately the shape of a circular disc and which has formed thereon a projection 41. The operating element 40 partially passes through the opening 16 in the housing (FIG. 1) whereby it is guided mechanically. On the side facing the printed circuit board 20 (FIG. 2–4), a centrally arranged pivot pin 44 is provided. This pivot pin is located in the eyelet 23 of the printed circuit board and the end section thereof is implemented such that it comprises two halves with an intermediate gap, whereby the ends of said pin 44 can be pressed together resiliently. In the assembled condition of the toggle switch, the pivot pin 44 is snapped in position in the eyelet 23 of the printed circuit board.

Furthermore, an inner driving pin 42 and an outer driving pin 43, which is displaced radially outwards relative to said inner driving pin 42, are provided on the side of the operating element 40 facing the printed circuit board 20. Between these driving pins a gap is provided, which corresponds approximately to the thickness of the strip-shaped sheet-metal spring 30 and the function of which will be described in detail hereinbelow in connection with the description of the mounting operation and the operation of the switch.

For limiting the rotation of the operating element 40 about the pivot pin 44 to an angular range of approx. 30° to 40°, stop means are provided, which extend on the outer periphery of the operating element in the axial direction and which abut on a front edge of the printed circuit board at the two stable positions of the switch.

In the following, it will first of all be explained how the toggle switch 50 is mounted on the printed circuit board of the device according to the present invention.

As has been explained hereinbefore, the toggle switch comprises only two parts, viz. the operating element 40 and the strip-shaped sheet-metal spring 30. The strip-shaped sheet-metal spring is forced into the gap between the driving pins 42, 43 of the operating element with one end piece thereof. The gap between the two driving pins is dimensioned precisely such that the strip- shaped sheet-metal spring 30 can be introduced between said pins in a slightly clamping condition. The strip-shaped sheet-metal spring will therefore adhere to the operating element without any further measures being required, and, consequently, said operating element can simultaneously be used as a mounting tool. The pivot pin 44 of the operating element 40 is then snapped in position in the eyelet 23 of the printed circuit board. When said pivot pin is being snapped in position, the switch occupies a position at which it is slightly more open than at the position shown in FIG. 4, i.e. the operating element 40 is rotated slightly more further to the left and the strip-shaped sheet-metal spring 30 has not yet come into locking engagement with the contact 22.

By rotating the operating element 40 to the right, the strip-shaped sheet-metal spring 30 is pushed over a detent projection of the contact 22 and comes there into locking engagement with an engagement trough. These simple measures already suffice to fully mount the switch.

In the following, it will now be described how the device according to the present invention is switched on and off, viz. how the toggle switch 50 moves between its two stable positions.

Taking as a basis the stable closed condition of the switch, which is shown in FIG. 2, the operating element 40 is rotated to the left and the driving pins 42, 43 slide along the ¾-circular bend of the strip-shaped sheet-metal spring upwards. This will have the effect that the distance a between the gap and the point where the strip-shaped sheet-metal spring abuts on the contact 22 will become smaller. The spring is resiliently pressed together due to the reduction of said distance a, and it reaches an unstable condition (FIG. 3).

When the operating element 40 is rotated to the left still further, the spring 30 will increasingly relax and distance a will enlarge (FIG. 4). During the rotation, the driving pins 42, 43 carry out an approximately circular movement about the axis of the operating element and they lift the strip-shaped sheet-metal spring 30 off the contact 21, whereby the electrically conductive connection between said contacts 21, 22 is interrupted. The stable, open condition of the toggle switch 50 has now been reached. A further rotary movement of the operating element 40 to the left is prevented by the stop means described hereinbefore.

The switch is closed by rotating the operating element to the right, whereby the conditions described hereinbefore will occur in the opposite sequence, as will easily be recognized by the person skilled in the art without any detailed explanations being required in this respect.

What is claimed is:

1. An electric device for evaporating substances, perfumes or the like, comprising a housing adapted to receive a receptacle containing said substance, an electric printed circuit board for a heating element said board being supported in said housing and a toggle switch including an actuation element which is adapted to be pivoted by a defined angle between two positions, a switching element for interrupting and for establishing an electrically conductive connection between two contacts and a resilient element co-operating with said switching element and said actuation element in such manner that the switching element takes up two stable switching positions and has unstable positions between the two stable ones, wherein said switching element and the resilient element are implemented as an integral strip-shaped sheet-metal spring, one end of said spring being held between two driving pins of the actuation element and the other end of said spring abutting one of said two contacts, said strip-shaped sheet-metal spring including a ¾-circular bend which is adapted to be brought into abutment with the other contact by pivoting the actuation element.

2. An electric device according to claim 1, wherein the other end is provided with a semi-circular opening snapped into locking engagement with a detent projection of one of said two contacts.

3. An electric device according to claim 1, wherein the two ends of said strip-shaped sheet-metal spring are bent off by approximately 90° at the ends of the ¾-circular bend.

4. An electric device according to claim 1, wherein said actuation element is supported in a receiving opening of the printed circuit board by a pivot pin formed on said board.

5. An electric device according to claim 4, wherein a central slot extending in the axial direction is provided at the free end of said pivot pin for forming two semi-cylindrical ends which are snapped into said receiving opening.

6. An electric device according to claim 4, wherein said electric printed circuit board is supported in the housing in such manner that the actuation element partially passes through an opening formed in said housing.

7. An electric device according to claim 1, wherein said contacts, adapted to be connected via the switching element, are arranged on said printed circuit board.

* * * * *